United States Patent [19]

Podraza et al.

[11] Patent Number: 4,540,004
[45] Date of Patent: Sep. 10, 1985

[54] SMOKING COMPOSITIONS CONTAINING A FLAVORANT-RELEASE ADDITIVE

[75] Inventors: Kenneth F. Podraza; Yoram Houminer, both of Richmond, Va.

[73] Assignee: Philip Morris, Incorporated, New York, N.Y.

[21] Appl. No.: 519,424

[22] Filed: Aug. 1, 1983

[51] Int. Cl.³ .......................... A24B 3/12; A24B 15/40
[52] U.S. Cl. .................................................... 131/277
[58] Field of Search ........................................ 131/277

[56] References Cited

U.S. PATENT DOCUMENTS

| | | |
|---|---|---|
| 3,332,428 | 7/1967 | Mold et al. |
| 3,419,543 | 12/1968 | Mold et al. |
| 3,499,452 | 3/1970 | Kallianos et al. |
| 4,092,988 | 6/1978 | Van Auken et al. |
| 4,119,106 | 10/1978 | Grubbs et al. |
| 4,177,339 | 12/1979 | Van Auken et al. |

Primary Examiner—V. Millin

[57] ABSTRACT

This invention provides smoking compositions which contain a tetracarbonate ester compound as a flavorant additive.

In one of its embodiments, this invention provides tobacco compositions which contain a tetracarbonate ester flavorant additive such as 2,5-bis(menthoxycarbonyloxymethylene)-3,6-bis(menthoxycarbonyloxy)-1,4-dioxane:

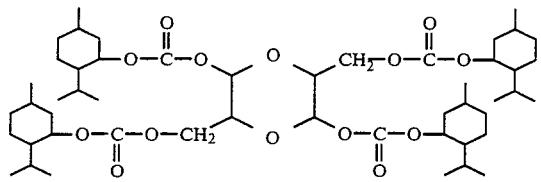

Under cigarette smoking conditions the above illustrated tetracarbonate ester pyrolyzes into menthol and other products which enhance the flavor of the mainstream smoke and the aroma of sidestream smoke.

7 Claims, No Drawings

SMOKING COMPOSITIONS CONTAINING A FLAVORANT-RELEASE ADDITIVE

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,722,516; 3,750,674; 3,879,425; 3,881,025; 3,884,247; 3,890,981; 3,903,900; 3,914,451; 3,915,175; 3,920,027; 3,924,644; 3,937,228; 3,943,943; 3,586,387; and the like.

The high degree of volatility and ease of sublimation of flavorant additives in tobacco products have presented problems in the manufacturing operations, and have resulted in a decreased shelf-life of the products due to losses of flavorant be evaporation on storage.

Recent developments have involved incorporating a low volatility organic additive to a smoking composition, which under smoking conditions is pyrolyzed into one or more fragments that function to improve the taste and character of mainstream tobacco smoke, and in some cases a consequential improvement of sidestream smoke aroma.

U.S. Pat. No. 3,312,226 describes smoking tobacco compositions which contain an ester additive such as 1-menthyl linalool carbonate. Under smoking conditions pyrolysis of the carbonate ester releases menthol which flavors the mainstream smoke.

U.S. Pat. Nos. 3,332,428 and 3,419,543 describe smoking tobacco compositions which contain a menthyl carbonate ester of a glycol or saccharide, which under smoking conditions decomposes to release free menthol into the mainstream smoke. U.S. Pat. No. 3,499,452 discloses similar smoking tobacco compositions in which a carbonate ester additive releases flavorant volatiles other than menthol.

U.S. Pat. No. 4,092,988 describes smoking tobacco compositions which contain a flavorant-release polymeric carbonate ester additive. Under smoking conditions the release of an olefinic pyrolyzate improves the flavor and aroma of mainstream and sidestream cigarette smoke.

U.S. Pat. Nos. 4,119,106; 4,171,702; 4,177,339; and 4,212,310 describe other oligomeric and polymeric carbonate ester derivatives which as constituents of smoking compositions are stable and non-volatile under storage conditions, and are adapted to release pyrolysis products under smoking conditions that improve the taste and aroma of the smoke.

There is continuing research effort to develop low delivery smoking compositions which generate mainstream smoke with enhanced taste and character under smoking conditions.

Accordingly, it is an object of this invention to provide smoking compositions having incorporated therein a flavorant component which is characterized by lack of mobility and/or volatility at ambient temperature.

It is another object of this invention to provide smoking tobacco compositions having incorporated therein a flavorant-release composition which under normal smoking conditions imparts improved flavor to mainstream smoke and improved aroma to sidestream smoke.

It is a further object of this invention to provide novel tetracarbonate ester compositions which are adapted to be incorporated into tobacco compositions, and which under normal smoking conditions release an alcohol or phenol type of volatile flavorant into cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and non-tobacco substitutes, and (2) between about 0.0001 and 2 weight percent, based on the total weight of filler, of a tetracarbonate ester flavorant-release additive corresponding to the formula:

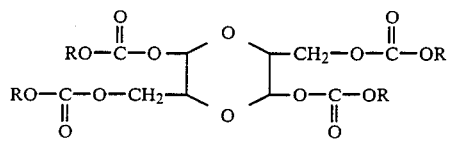

where R is a substituent selected from aliphatic, alicyclic and aromatic radicals.

In the ester formula represented above, the R substituent preferably is one containing between about 1–10 carbon atoms, such as methyl, ethyl, methoxyethyl, butyl, isobutyl, pentyl, 2-hexyl, 5-hexenyl, cyclohexyl, cyclohexenyl, menthyl, furfuryl, phenyl, tolyl, ethylphenyl, methoxyphenyl, ethoxyphenyl, hydroxyphenyl, and the like.

When a present invention smoking composition is subjected to normal smoking conditions such as with cigarettes, the tetracarbonate ester additive decomposes to release a volatile pyrolysis alcohol or phenol component which contributes flavor-enhancing properties to the mainstream smoke, such as for example:

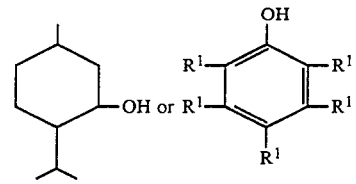

where $R^1$ is a substituent selected from hydrogen, alkyl, alkenyl and alkoxy groups containing between about 1–4 carbon atoms.

Because of the tetraester structure, a high yield of alcohol or phenol component is released from an invention tetracarbonate under pyrolysis conditions. Alcohols and phenols are a known class of tobacco flavorants, as reported by Leffingwell et al in a R. J. Reynolds publication (1972).

The present invention tetracarbonate esters are uniquely stable and odorless compounds at ambient temperatures. In addition, the tetracarbonate esters decompose at a relatively low pyrolysis temperature (e.g., 150°–300° C.) to release a high yield of desirable flavor-enhancing components in mainstream smoke.

PREPARATION OF TETRACARBONATE ESTERS

The tetracarbonate esters of the present invention can be prepared by reacting equivalent weights of a selected chloroformate compound with glyceraldehyde in the presence of a basic reagent. The reaction may be visualized as proceeding via in situ formed intermediates:

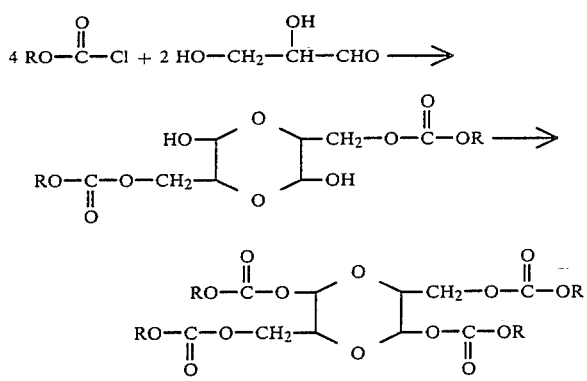

Details of organic carbonate ester synthesis are elaborated in prior art references such as U.S. Pat. Nos. 3,312,226 and 4,092,988. The present invention tetracarbonate esters are readily amenable to crystallization and chromatographic purification procedures.

As one of its embodiments, the present invention provides a novel class of tetracarbonate ester compositions corresponding to the formula:

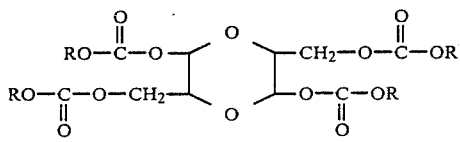

where R is a substituent selected from aliphatic, alicyclic and aromatic radicals. In addition to carbon and hydrogen, the R substituent can contain heteroatoms such as oxygen, nitrogen and sulfur.

PREPARATION OF TOBACCO COMPOSITIONS

In a further embodiment, the present invention provides a method of preparing a smoking composition which is adapted to impart improved taste and character to mainstream smoke under smoking conditions, which method comprises incorporating into natural tobacco and/or reconstituted tobacco and/or non-tobacco substitute between about 0.0001 and 2 weight percent, based on composition weight, of a tetracarbonate ester flavorant-release additive corresponding to the formula:

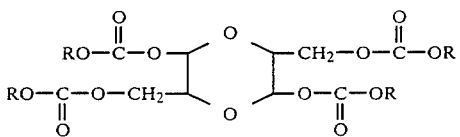

where R is a substituent selected from aliphatic, alicyclic and aromatic radicals.

The invention tetracarbonate ester flavorant-release additive can be incorporated into the tobacco in accordance with methods known and used in the art. Preferably the flavorant-release additive is dissolved in a solvent such as water, alcohol, or mixtures thereof, and then sprayed or injected into the tobacco and/or non-tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or non-tobacco substitute filler in a concentration between about 0.5–5 weight percent, based on the weight of filler, and then subsequently to blend the treated filler with filler which does not contain flavorant additive.

The term "non-tobacco substitute" is meant to include smoking filler materials such as are disclosed in U.S. Pat. Nos. 3,703,177; 3,796,222; 4,019,521; 4,079,742; and references cited therein, incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

The following Examples are further illustrative of the present invention. The specific ingredients and processing parameters are presented as being typical, and various modifications can be derived in view of the foregoing disclosure within the scope of the invention.

Examples I–IV illustrate the preparation of tetracarbonate ester compounds in accordance with the present invention. Infrared and nuclear magnetic resonance analyses are utilized to confirm the structure of each compound.

If the Examples I–IV type of tetracarbonate individually are incorporated into low delivery filtered cigarette tobacco fillers, there is a detectable enhancement of flavor and body in the mainstream smoke as compared to control cigarettes not containing a tetracarbonate flavorant-release additive.

EXAMPLE I 2,5-Bis(phenoxycarbonyloxymethylene)-3,6-bis-(phenoxycarbonyloxy)-1,4-dioxane

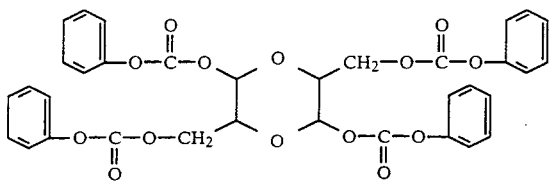

To a solution of 5 ml of pyridine in 50 ml of chloroform is added with stirring 1.0 g (0.0111 moles) of glyceraldehyde. The resulting suspension is chilled in an ice bath. A solution of 3.6 g (0.0222 moles) of phenyl chloroformate in 10 ml of chloroform is added dropwise. Stirring is continued for approximately 15 minutes while maintaining the temperature at 0° C., then for 18-24 hours at room temperature.

The solution is then heated with stirring at 40° C. for 1.5 hours, then for 1 hour at 60° C., after which time the solution is cooled to room temperature. The reaction mixture is washed with water, followed by aqueous saturated sodium bicarbonate. The organic layer is dryed over sodium sulfate. Evaporation of the solvent under reduced pressure yields a residual product mixture, to which toluene is added and removed by evaporation under reduced pressure. The semi-solid obtained is recrystallized from ethanol yielding 2.4 g of solid product, m.p. 155° C.

NMR and IR data confirm the above structure. Anal. calc. for $C_{34}H_{28}O_{14}$: C, 61,82; H, 4.27 Found: C, 61.64; H, 4.49.

EXAMPLE II 2,5-Bis(2-methoxy-4-methylphenoxycarbonyloxymethylene)-3,6-bis(2-methoxy-4-methylphenoxycarbonyloxy)-1,4-dioxane

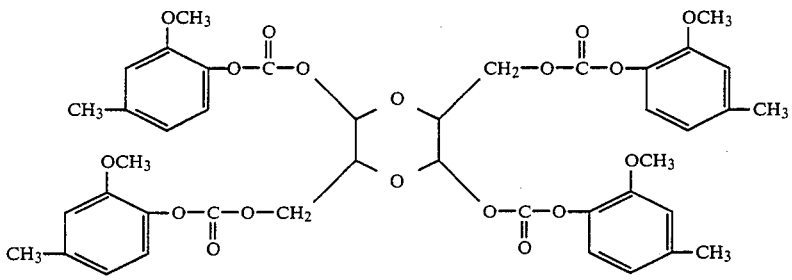

The synthesis of the title compound is conducted on a 0.0111 mole scale using glyceraldehyde and 2-methoxy-4-methylphenyl chloroformate, and the same conditions as described in Example I. The residual product mixture is recrystallized from chloroform/isooctane, yielding 3.2 g of solid product, m.p. 191°-192° C.

NMR and IR data confirm the above structure. Anal. calc. for $C_{42}H_{44}O_{18}$: C, 60.28; H, 5.30 Found: C, 60.13; H, 5.37.

EXAMPLE III 2,5-Bis(menthoxycarbonyloxymethylene)-3,6-bis(menthoxycarbonyloxy)-1,4-dioxane

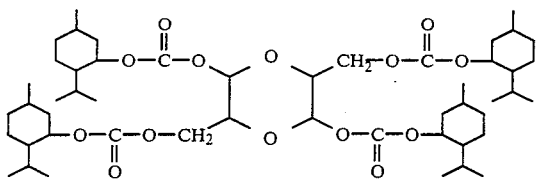

The synthesis of the title compound is conducted on a 0.0111 mole scale using glyceraldehyde and menthyl chloroformate, and the same conditions as described in Example I. The residual mixture is recrystallized from isopropanol, yielding 4.0 g of solid product, m.p. 139°-140° C.

NMR and IR data confirm the above structure. Anal. calc. for $C_{50}H_{84}O_{14}$: C, 66.05; H, 9.31 Found: C, 65.85; H, 9.46.

EXAMPLE IV 2,5-Bis(3-hexenoxycarbonyloxymethylene)-3,6-bis(3-hexenoxycarbonyloxy)-1,4-dioxane

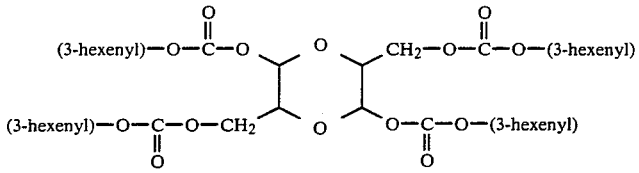

The synthesis of the title compound is conducted on a 0.0111 mole scale using glyceraldehyde and 3-hexenyl chloroformate, and the same conditions as described in Example I. The residual mixture is recrystallized from methanol, yielding 2.0 g of solid product, m.p. 68°-69° C.

NMR and IR data confirm the above structure. Anal. Calc. for $C_{34}H_{52}O_{14}$: C, 59.64; H, 7.65 Found: C, 59.40; H, 7.65.

What is claimed is:

1. A smoking composition comprising an admixture of (1) combustible filler selected from natural tobacco, reconstituted tobacco and non-tobacco substitutes, and (2) between about 0.0001 and 2 weight percent, based on the total weight of filler, of a tetracarbonate ester flavorant-release additive corresponding to the formula:

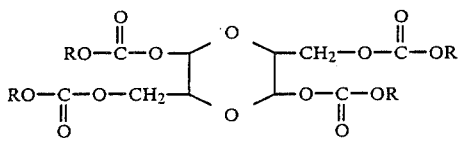

where R is a substituent selected from aliphatic, alicyclic and aromatic radicals.

2. A smoking composition in accordance with claim 1 wherein the non-tobacco substitutes are selected from pectinaceous, cellulosic and other carbohydrate materials.

3. A smoking composition in accordance with claim 1 wherein the tetracarbonate ester flavorant is 2,5-bis(-phenoxycarbonyloxymethylene)-3,6-bis(phenoxycarbonyloxy)-1,4-dioxane.

4. A smoking composition in accordance with claim 1 wherein the tetracarbonate ester flavorant is 2,5-bis(2-methoxy-4-methylphenoxycarbonyloxymethylene)-3,6-bis(2-methoxy-4-methylphenoxycarbonyloxy)-1,4-dioxane.

5. A smoking composition in accordance with claim 1 wherein the tetracarbonate ester flavorant is 2,5-bis(-menthoxycarbonyloxymethylene)-3,6-bis(menthoxycarbonyloxy)-1,4-dioxane.

6. A smoking composition in accordance with claim 1 wherein the tetracarbonate ester flavorant is 2,5-bis(3-hexenoxycarbonyloxymethylene)-3,6-bis(3-hexenoxycarbonyloxy)-1,4-dioxane.

7. A method of preparing a smoking composition which is adapted to impart flavoring to the mainstream and sidestream smoke under smoking conditions, which method comprises incorporating into natural tobacco, reconstituted tobacco or non-tobacco substitute between about 0.0001 and 2 weight percent, based on composition weight, of a tetracarbonate ester flavorant-release additive corresponding to the formula:

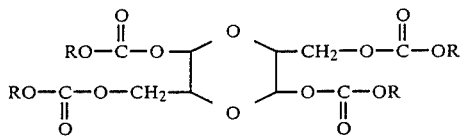

where R is a substituent selected from aliphatic, alicyclic and aromatic radicals.

* * * * *